US012797266B2

(12) United States Patent
Cheng

(10) Patent No.: US 12,797,266 B2
(45) Date of Patent: Nov. 17, 2026

(54) PAD FOR HUMAN BODY

(71) Applicants: Yi-Fu Cheng, Changhua City (TW); Hong-Jiun Cheng, Changhua City (TW); Aldwin Investment Co., Ltd., Changhua City (TW)

(72) Inventor: Meng-Song Cheng, Changhua City (TW)

(73) Assignees: Yi-Fu Cheng, Changhua City (TW); Hong-Jiun Cheng, Changhua City (TW); Aldwin Investment Co., Ltd., Changhua City (TW)

( * ) Notice: Subject to any disclaimer, the term of this patent is extended or adjusted under 35 U.S.C. 154(b) by 209 days.

(21) Appl. No.: 18/753,711

(22) Filed: Jun. 25, 2024

(65) Prior Publication Data

US 2025/0107948 A1 Apr. 3, 2025

(30) Foreign Application Priority Data

Sep. 28, 2023 (TW) ................................ 112137524

(51) Int. Cl.
*A61F 13/84* (2006.01)
*A61F 13/472* (2006.01)

(52) U.S. Cl.
CPC ............ *A61F 13/84* (2013.01); *A61F 13/472* (2013.01)

(58) Field of Classification Search
CPC .................. A61F 13/84; A61F 13/8405; A61F 2013/5105; A61F 2013/530328; A61F 2013/53; A61F 2013/671; A61F 2013/8423; A61F 2013/8426; A61F 2013/8429; A61K 33/06; A61K 33/08; A61K 33/10; A61K 33/12; A61L 15/18
See application file for complete search history.

(56) References Cited

U.S. PATENT DOCUMENTS 5,419,956 A * 5/1995 Roe ....................... A61F 13/535 428/326
6,610,780 B1 * 8/2003 Payzant .................. B01J 20/30 524/789
9,072,806 B2 * 7/2015 Lo .......................... A61L 15/28
9,814,798 B2 * 11/2017 Cordeiro Bastos ..... A61L 15/22
(Continued)

FOREIGN PATENT DOCUMENTS

| | | |
|---|---|---|
| EP | 1937199 B1 | 3/2013 |
| EP | 2583647 A1 | 4/2013 |
| RU | 2620856 C1 | 5/2017 |

OTHER PUBLICATIONS

Search Report issued to European counterpart application No. 24201172.4 by the EPO on Mar. 5, 2025.

*Primary Examiner* — Catharine L Anderson
(74) *Attorney, Agent, or Firm* — MUNCY, GEISSLER, OLDS & LOWE, P.C.

(57) ABSTRACT

A pad for a human body includes a sheet body that has a first surface and a second surface opposite to the first surface, and that includes fibers. Each of the fibers includes a polymer substrate and pyroelectric materials distributed on the polymer substrate. The pyroelectric materials and the polymer substrate are polarized under an electric field. Each of the pyroelectric materials exhibits infrared absorption peaks at 1460 $cm^{-1}$, 1165 $cm^{-1}$, 1090 $cm^{-1}$, 968 $cm^{-1}$, and 720 $cm^{-1}$.

10 Claims, 8 Drawing Sheets

(56) References Cited

U.S. PATENT DOCUMENTS

| | | | | |
|---|---|---|---|---|
| 2003/0133990 | A1* | 7/2003 | Hursey | A61L 15/18 424/617 |
| 2011/0064787 | A1* | 3/2011 | Cabados | A61K 9/7023 424/447 |
| 2016/0076170 | A1* | 3/2016 | Blaney | B32B 5/08 428/401 |
| 2018/0000092 | A1* | 1/2018 | Crouch | A01N 59/16 |
| 2021/0189603 | A1* | 6/2021 | Horinek | D01F 1/106 |
| 2024/0299769 | A1* | 9/2024 | Vissman | A61N 5/06 |
| 2025/0127952 | A1* | 4/2025 | Kumar | A61L 15/60 |

* cited by examiner

PAD FOR HUMAN BODY

CROSS-REFERENCE TO RELATED APPLICATION

This application claims priority to Taiwanese Invention Patent Application No. 112137524, filed on Sep. 28, 2023, the entire disclosure of which is incorporated by reference herein.

FIELD

The present disclosure relates to a pad, and more particularly to a pad for a human body.

BACKGROUND

Women are prone to urine leakage due to pregnancy, childbirth, menopause, and the inherent structure of the female urinary tract. Meanwhile, as men grow older, issues related to prostatic hyperplasia due to tissue proliferation are quite common. In addition, modern sedentary lifestyles or constipation can lead to congestion of blood vessels near an anus, thereby reducing venous return and increasing the likelihood of hemorrhoid development. Furthermore, prolonged bedridden patients may experience bedsores due to skin compression and poor blood circulation. The aforesaid symptoms may plague patients for a long time and even affect their daily lives.

In view of the aforesaid, there is still a need to develop a pad for a human body that can reduce discomfort caused by the aforesaid symptoms due to poor blood circulation or muscle relaxation in tissues around a pelvic cavity.

SUMMARY

Therefore, an object of the present disclosure is to provide a pad for a human body, which can alleviate at least one of the drawbacks of the prior art.

According to the present disclosure, the pad includes a sheet body that has a first surface and a second surface opposite to the first surface, and that includes fibers. Each of the fibers includes a polymer substrate and pyroelectric materials distributed on the polymer substrate. The pyroelectric materials and the polymer substrate are polarized under an electric field. Each of the pyroelectric materials exhibits infrared absorption peaks at 1460 $cm^{-1}$, 1165 $cm^{-1}$, 1090 $cm^{-1}$, 968 $cm^{-1}$, and 720 $cm^{-1}$.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

<Pad for Human Body>

Figure 1:
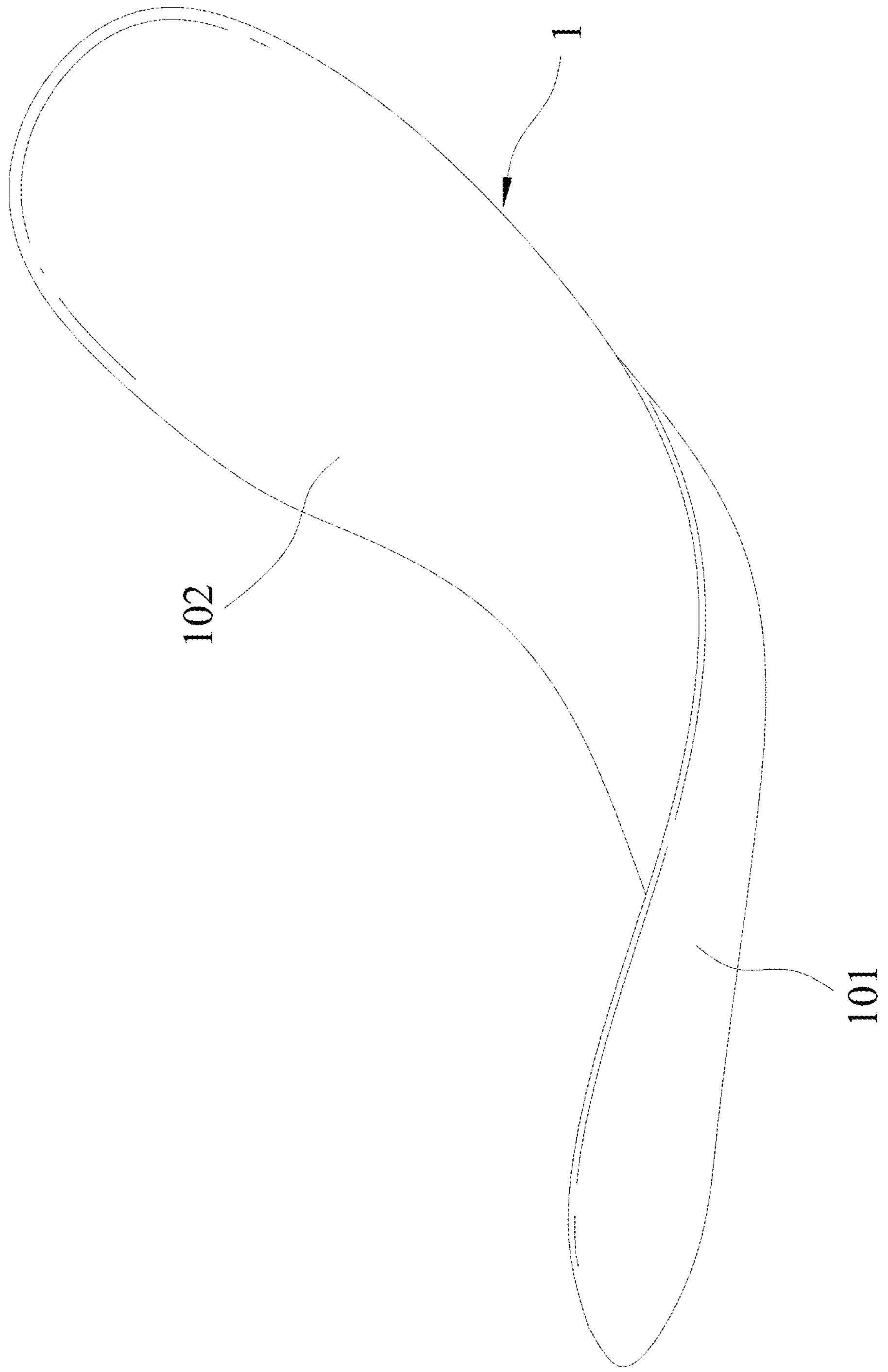
FIG. 1 is a perspective view showing an embodiment of a pad for a human body according to the present disclosure.
Figure 2:
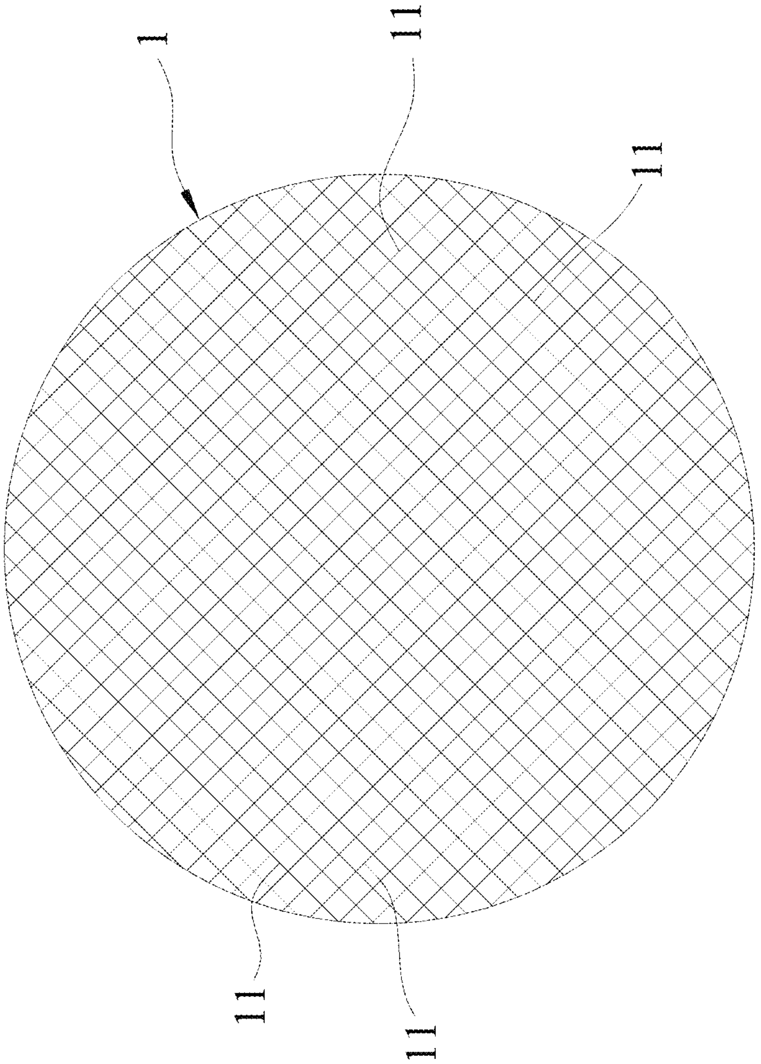
FIG. 2 is a partially enlarged view of the embodiment.
Figure 3:
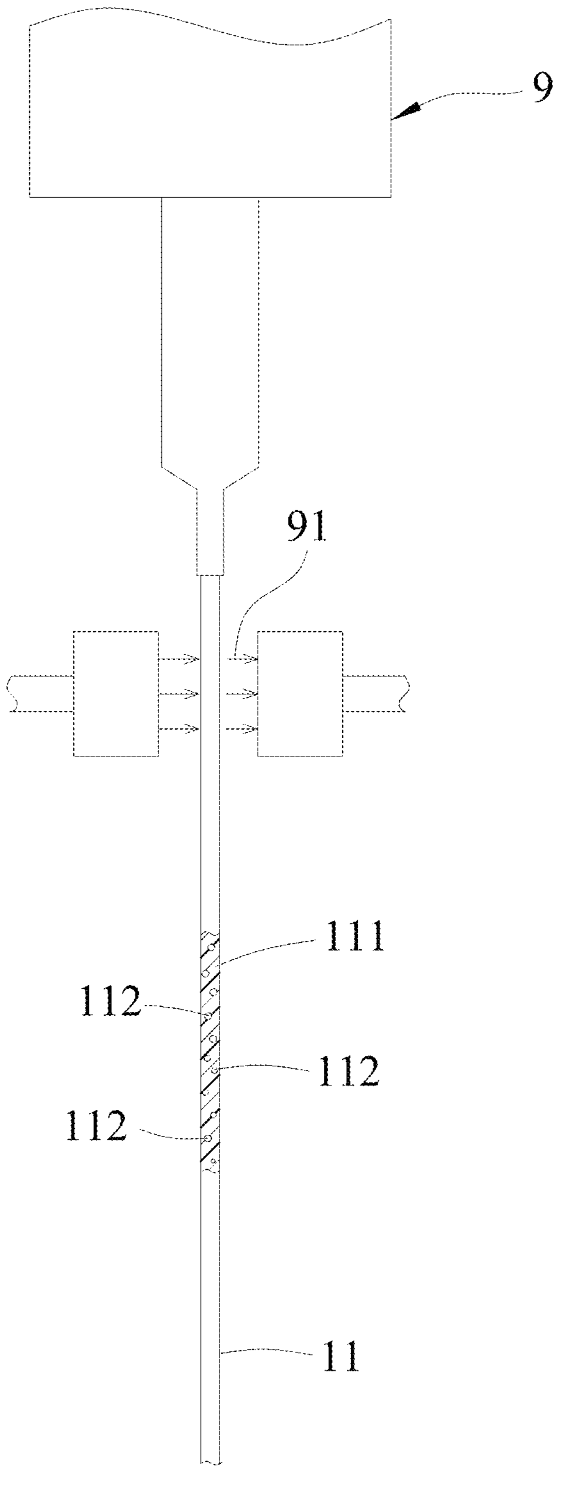
FIG. 3 is a schematic diagram showing a manufacturing process of the embodiment.
Figure 4:
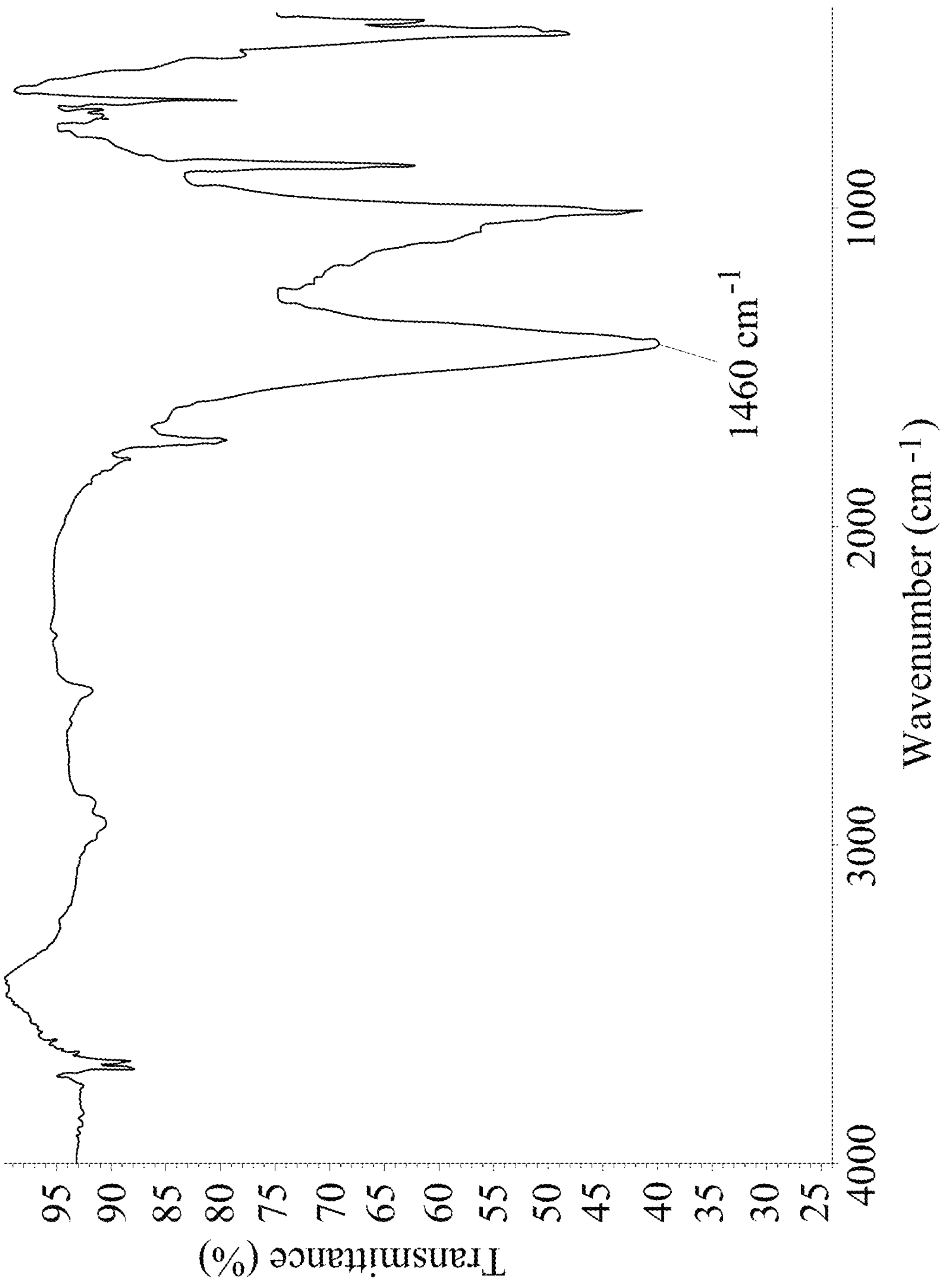
FIG. 4 is a graph showing the transmission Fourier-transform infrared (FTIR) spectra for kaolin.
Figure 5:
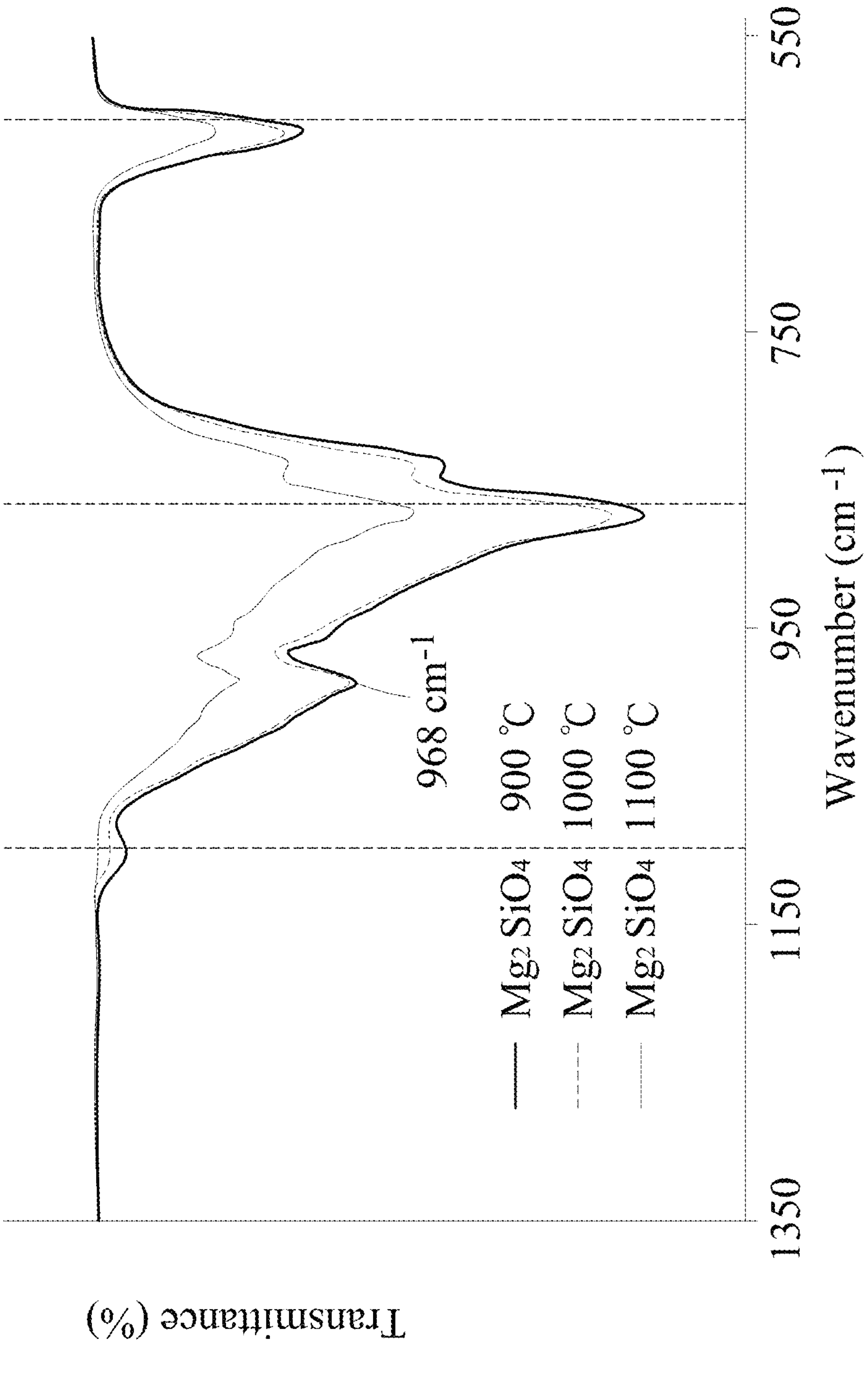
FIG. 5 is a graph showing the transmission FTIR spectra for forsterite.
Figure 6:
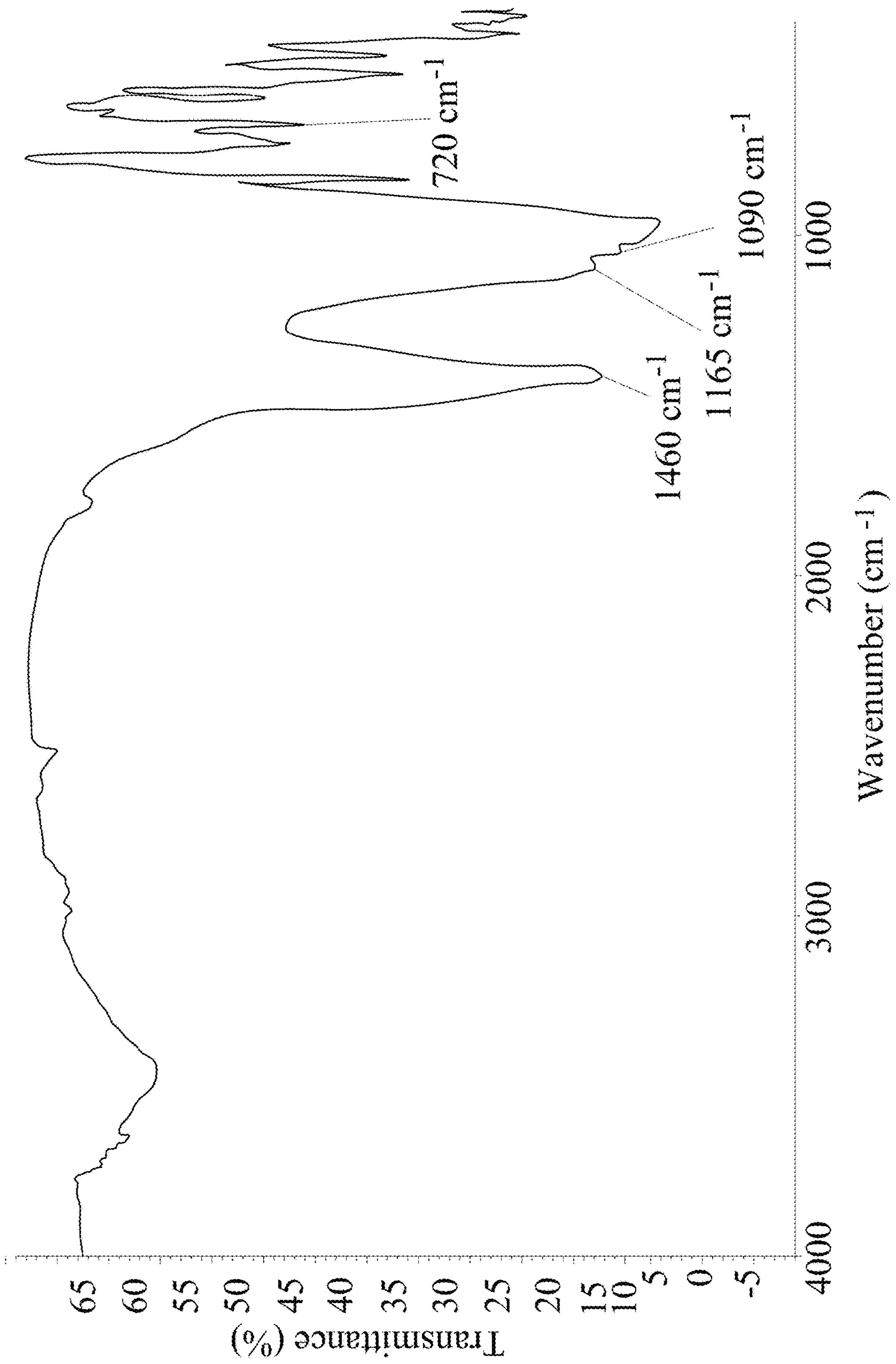
FIG. 6 is a graph showing the transmission FTIR spectra for maifan stone.
Figure 7:
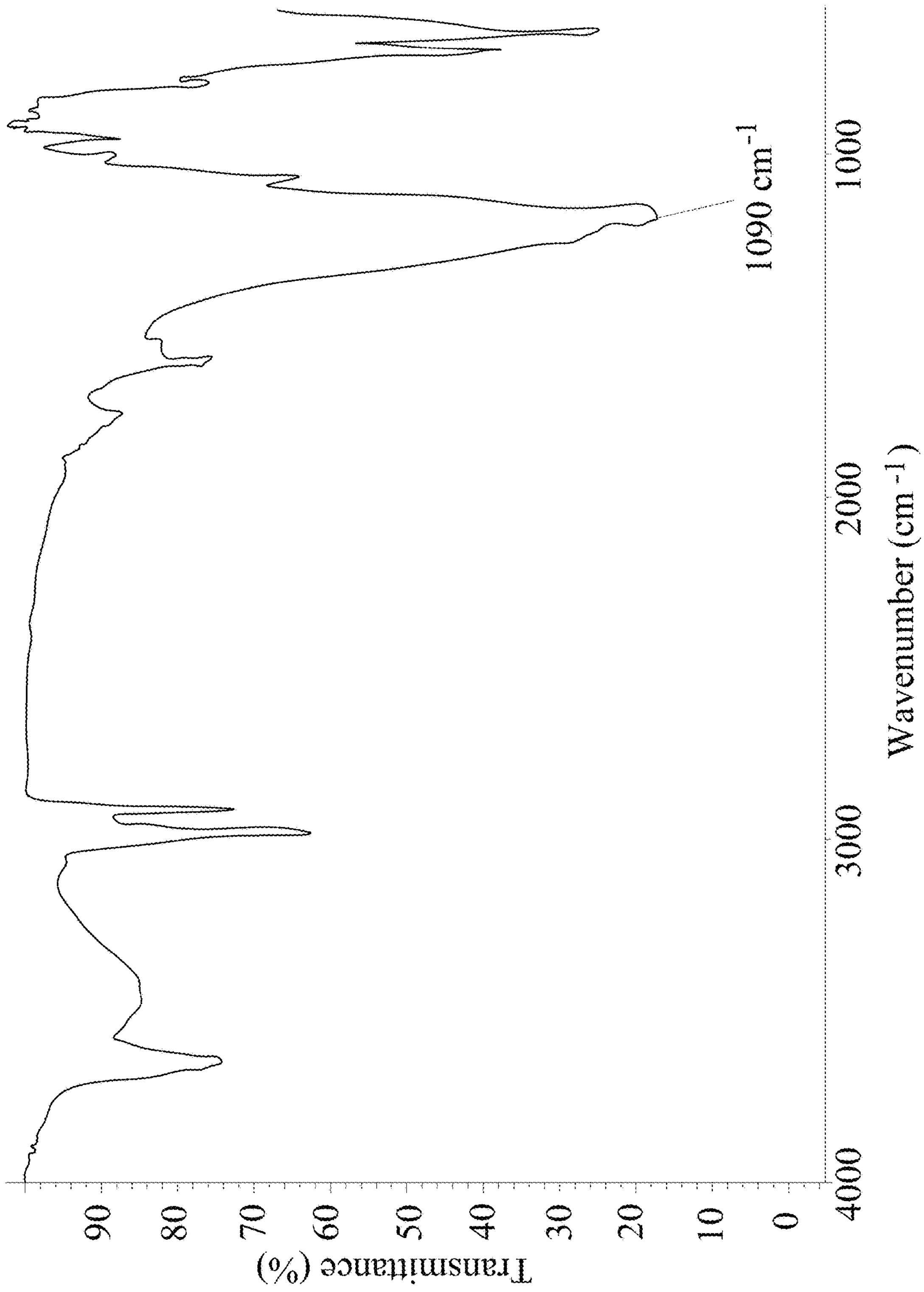
FIG. 7 is a graph showing the transmission FTIR spectra for montmorillonite.
Figure 8:
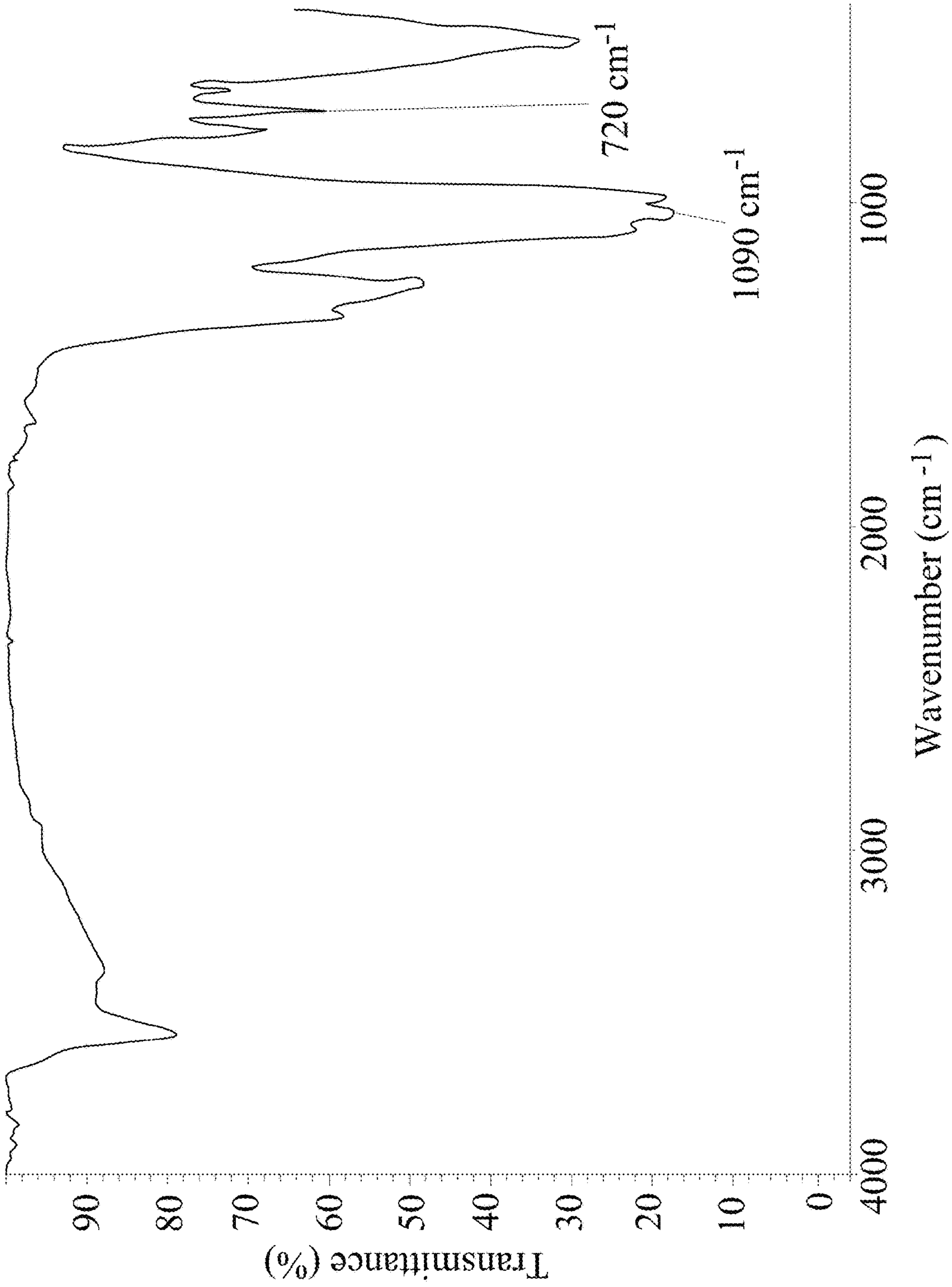
FIG. 8 is a graph showing the transmission FTIR spectra for tourmaline.

Referring to FIGS. 1 to 3, a pad for a human body according to an embodiment of the present disclosure includes a sheet body 1. The pad is primarily intended to be placed around the human body's pelvic cavity or for use inside underpants, so that the sheet body 1, which is close-fitting, is in direct contact with the skin of the human body.

According to the present disclosure, the sheet body 1 includes fibers 11, and has a first surface 101 and a second surface 102 opposite to the first surface 101. In certain embodiments, the sheet body 1 is a woven fabric made by spinning and weaving the fibers 11. In other embodiments, the sheet body 1 is a non-woven fabric in which the fibers 11 are directly bonded under high pressure without spinning, so that the fibers 11 are irregularly arranged. In addition, the shape, size, and thickness of the sheet body 1 are not particularly limited, and can vary according to a human body part or wound size on which the pad is intended to be used.

According to the present disclosure, each of the fibers 11 includes a polymer substrate 111, pyroelectric materials 112 distributed on the polymer substrate 111, and coupling agents (not shown) distributed on the polymer substrate 111. In certain embodiments, the polymer substrate 111 is an aliphatic polyamide, and the aliphatic polyamide is nylon 6 (polycaprolactam) which has polarity. In certain embodiments, the fibers 11 are formed by uniformly mixing solid plastic particles of polymerized nylon 6 and a fine powder of the pyroelectric materials 112 in a solid state, followed by conducting a melt spinning process using a screw spinning machine 9 and a polarization process.

According to the present disclosure, the pyroelectric materials 112 are present in an amount ranging from 1 wt % to 3 wt % based on the total weight of each of the fibers 11, and each of the pyroelectric materials 112 contains kaolin, forsterite (a main component thereof is $Mg_2SiO_4$), and maifan stone. In this embodiment, the pyroelectric materials 112 are present in an amount of 1.8 wt % based on the total weight of each of the fibers 11, and each of the pyroelectric materials 112 contains kaolin, forsterite, maifan stone, montmorillonite, and tourmaline. In certain embodiments, kaolin is present in an amount of 50 wt %, forsterite is present in an amount of 20 wt %, maifan stone is present in an amount of 10 wt %, montmorillonite is present in an amount of 10 wt %, and tourmaline is present in an amount of 10 wt %, based on the total weight of each of the pyroelectric materials 112. In certain embodiments, the pyroelectric materials 112 may be a powder, fine flakes, or fine particles, and each of the pyroelectric materials 112 has a mean surface width or a mean particle size of 1 μm.

According to the present disclosure, the pyroelectric materials 112 and the polymer substrate 111 have polarity and are polarized under an electric field 91. In this embodiment, the polymer substrate 111 and the pyroelectric materials 112 have pyroelectric properties, and thus releases negative charges after being heated. Each of the pyroelectric materials 112 exhibits infrared absorption peaks at 1460 $cm^{-1}$, 1165 $cm^{-1}$, 1090 $cm^{-1}$, 968 $cm^{-1}$, and 720 $cm^{-1}$. The polymer substrate 111 is the nylon 6, and exhibits infrared absorption peaks ranging from 720 $cm^{-1}$ to 980 $cm^{-1}$. The molecular chain of the nylon 6 includes a polar amide group (CO—NH), is a highly crystalline linear polymer with an ability to form hydrogen bonds between molecular chains, and has dipole moments that can be strengthened after polarization under the electric field 91. In other embodiments, the polymer substrate 111 may be polyester fiber (i.e., polyethylene terephthalate (PET)), or polypropylene (PP) fiber.

Referring to FIGS. 4 to 8, each of the kaolin and the maifan stone exhibits an infrared absorption peak at 1460 $cm^{-1}$; the maifan stone exhibits an infrared absorption peak at 1165 $cm^{-1}$; each of the montmorillonite, the maifan stone, and the tourmaline exhibits an infrared absorption peak at 1090 $cm^{-1}$; the forsterite exhibits an infrared absorption peak at 968 $cm^{-1}$; and each of the maifan stone and the tourmaline exhibits an infrared absorption peak at 720 $cm^{-1}$.

<Manufacturing Process for Preparing Pad for Human Body>

In certain embodiments, the aforesaid pad of the present disclosure is prepared according to a manufacturing process described below. First, the kaolin, the forsterite, the maifan stone, the montmorillonite, and the tourmaline are mixed together to obtain a raw material for the pyroelectric materials 112, followed by pulverizing using a pulverizer, so as to obtain coarse powders each having a mean surface width of 5 μm. Then, the coarse powders are subjected to magnetic separation using a magnetic separator with a magnetic flux density of 1.5 Tesla (T), followed by fine grinding using a grinder, so as to obtain fine powders each having a mean surface width or a mean particle size of 1 μm. Thereafter, the fine powders are polarized under an electric field strength of $1.2\times10^{8}$ V/m, followed by washing and purifying with water, and finally dehydrating and drying, so as to obtain the pyroelectric materials 112.

Next, the resultant dried fine powders (i.e., the pyroelectric materials 112) and the solid plastic particles of the polymerized nylon 6 (serving as the polymer substrate 111) are uniformly mixed with each other in a solid state, followed by mixing with coupling agents, so as to form a mixture. Since the dried fine powders and the solid plastic particles of the polymerized nylon 6 are mixed in the solid state without being influenced by viscosity thereof, uniformity of the mixing can be increased.

Subsequently, the aforesaid mixture is heated and subjected to a melt-spinning process using the screw spinning machine 9 to form the fibers 11. During the melt spinning process, the mixture is polarized under an electric field strength ranging from $3.0\times10^{6}$ V/m to $7.0\times10^{6}$ V/m, so that dipole moments of the fibers 11 can be regularly arranged parallel to a direction of the electric field 91, resulting in increased strength of dipole moments thereof to obtain more pronounced hysteresis loop, so as to increase an energy of releasing charges. In certain embodiments, during the melt spinning process, the mixture is polarized under an electric field strength of $7.0\times10^{6}$ V/m, so as to form each of the fibers 11.

Finally, the fibers 11 are spun and woven, followed by cutting into a sheet body 1, so that the sheet body 1 can be directly used. In certain embodiments, the sheet 1 may be a non-woven fabric, or may further include a positioning element (not shown), such as a double-sided tape, that is disposed on the first surface 101 of the sheet body 1 to enhance a positioning effect during use.

The disclosure will be further described by way of the following examples. However, it should be understood that the following examples are solely intended for the purpose of illustration and should not be construed as limiting the disclosure in practice.

EXAMPLES

Preparation of Pad for a Human Body

A pad for a human body according to the present disclosure was prepared in accordance to the manufacturing process as described above, and was evaluated as described in the following Examples 1 to 6 (EX1 to EX6).

Evaluation of Therapeutic Effect

Example 1 (EX1): Evaluation for the Effect of the Pad According to the Disclosure in Alleviating Bedsore A sheet body 1 of a pad was placed inside underpants of a user suffering from bedsore, and the pad was replaced with a new pad on a daily basis. Thereafter, a healing state of an affected region of the user was observed as a criterion for evaluation. The user and a usage situation of EX1 are described as follows.

User A, a 93-year-old man named Chen, had bedsore on his buttocks and had been hospitalized for six months without any improvement. After two weeks of continuous use of pads, a 70% reduction in a size of the bedsore in the affected region (i.e., User A's buttocks) was observed. After four weeks of continuous use of the pads, the bedsore in the affected region was completely healed. In addition, User A's buttocks had regained elasticity. These results indicate that the pad of the present disclosure can enhance blood circulation in tissues around a pelvic cavity and improve a function of a pelvic muscle.

Example 2 (EX2): Evaluation for the Effect of the Pad According to the Disclosure in Alleviating Urine Leakage A pad according to the disclosure was provided to different users each having urine leakage problem. The pad was placed inside underpants of each of the users and replaced with a new pad on a daily basis. A dryness level of a sheet body 1 of the pad for each of the users after daily use was observed as a criterion for evaluation. The users and usage situations of EX2 are described as follows.

User B, a 56-year-old woman named Lin, had been using commercially available sanitary pads for a long time due to urine leakage problem. After the first day of use, a sheet body 1 was slightly damp. After the second day of use, another sheet body 1 was slightly damp. However, after the third day of use, still another sheet body 1 was completely dry. After one month, User B no longer experienced urine leakage, even during intense physical activity.

User C, a 70-year-old woman named Lin, had been using commercially available sanitary pads for a long time due to urine leakage problem. After the first day of use, a sheet body 1 was slightly damp. After the second day of use, another sheet body 1 was slightly damp. However, after the third day of use, still another sheet body 1 was completely dry. Currently, User C does not have urine leakage problem.

User D, a 50-year-old woman named Zhan, suffered from urine leakage problem. After the first day of use, a sheet body 1 was completely dry, and the urine leakage was already significantly alleviated. Currently, User D does not have urine leakage problem.

User E, a 90-year-old woman named Zheng, had 8 daughters and 1 son with severe urine leakage problem. After three days of use, a sheet body 1 was completely dry, and the urine leakage was already significantly alleviated. Currently, User E does not have urine leakage problem.

User F, a 65-year-old woman named Zheng, had 1 daughter and 1 son, and had suffered from urine leakage problem for a long time. On the fourth day of use, a sheet body 1 was slightly damp. On the fifth day of use, another sheet body 1 was completely dry. Currently, User F does not have urine leakage problem.

Example 3 (EX3): Evaluation for the Effect of the Pad According to the Disclosure in Alleviating Hemorrhoid A sheet body 1 of a pad was placed inside underpants of each of users suffering from hemorrhoid, and the pad was replaced with a new pad on a daily basis. Thereafter, an appearance of an affected region of each of the users was observed as a criterion for evaluation. The users and usage situations of EX3 are described as follows.

User G, a 40-year-old man named Huang, suffered from hemorrhoid in his anus. After five days of continuous use of pads, the affected region was observed and the hemorrhoid in the affected region was completely healed.

User H, a 45-year-old man named Chen, suffered from hemorrhoid in his anus. After seven days of continuous use of pads, the affected region was observed and the hemorrhoid in the affected region was completely healed.

Example 4 (EX4): Evaluation for the Effect of the Pad According to the Disclosure in Alleviating Prostatitis A sheet body 1 of a pad was placed inside underpants of each of users suffering from prostatitis, and the pad was replaced with a new pad on a daily basis. Thereafter, a frequency of nocturia of the users was observed as a criterion for evaluation. The users and usage situations of EX4 are described as follows.

User I, an 85-year-old man, frequently urinated up to 5 times at night due to the prostatitis. After one month of continuous use of pads, the frequency of nocturia was reduced to 1 time, and nocturia was already significantly alleviated.

User J, a 50-year-old man named Chen, suffered from weak urine stream due to the prostatitis and thus spent a long time to urinate. After two days of continuous use of pads, a duration of urination was significantly reduced.

Example 5 (EX5): Evaluation for the Effect of the Pad According to the Disclosure in Alleviating Urinary Incontinence A sheet body 1 of a pad was placed inside underpants of a user suffering from urinary incontinence, and the pad was replaced with a new pad on a daily basis. Thereafter, a frequency of nocturia of the user was observed as a criterion for evaluation. The user and a usage situation of EX5 are described as follows.

User K, an 81-year-old woman named Gao, had urinary incontinence for a long time, with up to 4 or 5 urination episodes per day at night. The episode of nocturia on the first day of using a pad was 1, on the second day of using another pad was 2, and on the third day of using still another pad was 1, and User K was thus able to control urinary incontinence.

Example 6 (EX6): Evaluation for the Effect of the Pad According to the Disclosure in Alleviating a Gynecological Disease A sheet body 1 of a pad was placed inside underpants of a user suffering from a gynecological disease, and the pad was replaced with a new pad on a daily basis. Thereafter, an amount of vaginal discharge of the user was observed as a criterion for evaluation. The user and a usage situation of EX6 are described as follows.

User L, a 38-year-old woman named Xiao, was troubled by vaginal discharge after natural birth. On the first day of using a pad, the amount of the vaginal discharge was unchanged. On the second day of using another pad, the amount of the vaginal discharge became less. On the third day of using still another pad, there was no vaginal discharge. From the fourth day on, it is unnecessary to use a sheet body 1 of yet another pad.

Summarizing the above test results of using the pad to evaluate the therapeutic effect for EX1 to EX6, it is clear that by virtue of the pyroelectric materials 112 exhibiting infrared absorption peaks at 1460 $cm^{-1}$, 1165 $cm^{-1}$, 1090 $cm^{-1}$, 968 $cm^{-1}$, and 720 $cm^{-1}$, the sheet body 1 of the present disclosure is capable of increasing an efficiency of electron absorption and eliminating free radicals in a human body to alleviate an inflammatory response, thereby enhancing blood circulation in tissues around a pelvic cavity, improving the function of the pelvic muscle and reducing discomfort, such as urine leakage, urinary incontinence, or vaginal relaxation, that is caused by poor blood circulation or muscle relaxation in the tissues around the pelvic cavity. Therefore, the pad of the present disclosure for a human body can indeed achieve the object thereof.

Evaluation of Antibacterial Activity

The sheet body 1 of the present disclosure was sent to a testing organization, TÜV SÜD Products Testing (Shanghai) Co., Ltd, and was subjected to determination of antibacterial activity value (A) for *Staphylococcus aureus* (ATCC 6538), *Escherichia coli* (ATCC 8739), and *Candida albicans* (ATCC 10231) in accordance with ISO 20743:2021, so as to determine the antibacterial activity of the sheet body 1. An antibacterial activity value (A) of less than 2 indicated weak antibacterial activity in a sample. An antibacterial activity value (A) of not less than 2 but less than 3 indicated significant antibacterial activity in a sample. An antibacterial activity value (A) of not less than 3 indicated strong antibacterial activity in a sample. The test results showed that the antibacterial activity value (A) of the sheet body 1 of the present disclosure for *Staphylococcus aureus, Escherichia coli*, and *Candida albicans* were 5.7, 6.2, and 4.7, respectively. These results demonstrate that the sheet body 1 of the present disclosure has strong antibacterial activity.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, the one or more features may be singled out and practiced alone without the another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A pad for a human body, comprising a sheet body that has a first surface and a second surface opposite to the first surface, and that includes fibers, each of the fibers including a polymer substrate and pyroelectric materials distributed on the polymer substrate, the pyroelectric materials and the polymer substrate being polarized under an electric field, wherein each of the pyroelectric materials contains kaolin, forsterite, and maifan stone, and exhibits infrared absorption peaks at 1460 $cm^{-1}$ attributed to the kaolin and the maifan stone, 1165 $cm^{-1}$ attributed to the maifan stone, 1090 $cm^{-1}$ attributed to the maifan stone, 968 $cm^{-1}$ attributed to the forsterite, and 720 $cm^{-1}$ attributed to the maifan stone.

2. The pad as claimed in claim 1, wherein the pyroelectric materials are present in an amount ranging from 1 wt % to 3 wt % based on the total weight of each of the fibers.

3. The pad as claimed in claim 2, wherein the pyroelectric materials are present in an amount of 1.8 wt % based on the total weight of each of the fibers, each of the pyroelectric materials further containing montmorillonite which exhibits an infrared absorption peak at 1090 $cm^{-1}$ and tourmaline which exhibits infrared absorption peaks at 1090 $cm^{-1}$ and 720 $cm^{-1}$.

4. The pad as claimed in claim 1, wherein each of the fibers further includes coupling agents distributed on the polymer substrate.

5. The pad as claimed in claim 1, wherein the sheet body is a woven fabric in which the fibers are woven or the sheet body is a non-woven fabric in which the fibers are irregularly arranged.

6. The pad as claimed in claim 1, wherein each of the pyroelectric materials has a mean surface width or a mean particle size of 1 μm.

7. The pad as claimed in claim 1, wherein the polymer substrate is an aliphatic polyamide, the aliphatic polyamide being nylon 6 which has polarity.

8. The pad as claimed in claim 7, wherein each of the fibers are formed by mixing the polymer substrate and the pyroelectric materials in a solid state, followed by conducting a melt spinning process and a polarization process.

9. The pad as claimed in claim 1, wherein the pyroelectric materials are formed by conducting a polarization process under an electric field strength of $1.2\times10^{8}$ V/m, and each of the fibers are formed by mixing the pyroelectric materials and the polymer substrate in a solid state, followed by conducting a melt spinning process and a polarization process which is performed under an electric field strength of $7.0\times10^{6}$ V/m.

10. The pad as claimed in claim 1, further comprising a positioning element disposed on the first surface of the sheet body.

* * * * *